United States Patent
Bille et al.

(10) Patent No.: US 7,844,425 B2
(45) Date of Patent: Nov. 30, 2010

(54) FINITE ELEMENT MODELING OF THE CORNEA

(75) Inventors: Josef F. Bille, Heidelberg (DE); Luis Antonio Ruiz, Bogotá (CO); Frieder Loesel, Mannheim (DE)

(73) Assignee: Technolas Perfect Vision GmbH, Munich (DE)

( * ) Notice: Subject to any disclaimer, the term of this patent is extended or adjusted under 35 U.S.C. 154(b) by 331 days.

(21) Appl. No.: 12/016,857

(22) Filed: Jan. 18, 2008

(65) Prior Publication Data

US 2009/0187386 A1 Jul. 23, 2009

(51) Int. Cl.
*G06F 17/10* (2006.01)
*G06G 7/60* (2006.01)
(52) U.S. Cl. .......................... 703/2; 703/11
(58) Field of Classification Search ............. 703/2, 703/11; 606/5
See application file for complete search history.

(56) References Cited

U.S. PATENT DOCUMENTS

| | | | | |
|---|---|---|---|---|
| 7,130,835 | B2* | 10/2006 | Cox et al. | 706/21 |
| 2003/0208190 | A1* | 11/2003 | Roberts et al. | 606/5 |
| 2009/0187387 | A1* | 7/2009 | Bille | 703/2 |
| 2009/0318907 | A1* | 12/2009 | Bille et al. | 606/5 |

OTHER PUBLICATIONS

Hollman et al., K.W. Strain Imaging of Corneal Tissue with an Ultrasound Elasticity Microscope, Cornea:, Jan. 2002, vol. 21, Iss. 1, pp. 68-73.*

Database Compendex [Online], Engineering Information, Inc., New York, US; XIE J-Z et al: "Analytic modeling and simulating of the cornea with finite element method" XP002519239, Database accession No. E20082711349193 abstract & Lecture Notes in Computer Science (Including Subseries Lecture Notes in Artificial Intelligence and Lecture Notes in Bioinformatics)—Medical Imaging and Informatics—2nd International Conference, Mimi 2007, Revised Selected Papers 2008.

Database Medline [Online] US National Library of Medicine (NLM), Bethesda, MD, US; Jan. 2002, Hollman Kyle W et al: "Strain imaging of corneal tissue with an ultrasound elasticity microscope." XP002519240, Database accession No. NLM11805511 abstract & CORNEA Jan. 2002, vol. 21, No. 1, Jan. 2002, pp. 68-73, ISSN: 0277-3740, Section: Direct Mechanical Elasticity and Finite Element Model.

Database Medline [Online] US National Library of Medicine (NLM), Bethesda, MD, US: Feb. 1998, Hennighausen H et al: "Anterior-posterior strain variation in normally hydrated and swollen rabbit cornea." XP002519241 Database accession No. NLM9477981 abstract & Investigative Ophthalmology & Visual Science Feb. 1998, vol. 39, No. 2, Feb. 1998, pp. 253-262, ISSN: 0146-0404, Section: Image and Data Analasis the whole document.

(Continued)

*Primary Examiner*—Russell Frejd
(74) *Attorney, Agent, or Firm*—Nydegger & Associates

(57) ABSTRACT

A system and method for simulating a corneal reconfiguration in response to LIOB uses a computer-programmed, finite element model. The model has a plurality of elements; with each element pre-programmed with coefficients based on diagnostic corneal data. Collectively the coefficients replicate biomechanical properties of the cornea. In use, designated biomechanical characteristics on a plurality of selected elements (i.e. selected coefficients) are minimized to simulate LIOB in an actual cornea. A computer then measures the resultant reconfiguration of the cornea model to assess an actual cornea's response to LIOB.

15 Claims, 2 Drawing Sheets

OTHER PUBLICATIONS

Ruiz, L. A., MD. "Preliminary clinical results of non-invasive, intrastromal correction of presbyopia using the FEMTEC femtosecond laser system", Hawaiian Eye Meeting (2008).

Anderson, K., El-Sheikh, A., & Newson, T., "Application of structural analysis to the mechanical behaviour of the cornea", The Royal Society, (2004).

Anderson, K., El-Sheikh, A., & Newson, T., "FEA of the biomechanics of procine corneas", The Structural Engineer, (2004).

Crouch, Jessica R., Merriam, John C., and Crouch, Earl R. "Finite Element Model of Cornea Deformation." Medical Image Computing and Computer-Assisted Intervention. Springer Berlin. Heidelberg, Germany, 2005. 591-598.

Scherer, K.,P., Eggert, H., Guth, H., and Stiller, P., "Biomechanical simulations for refractive corneal eye surgery", Proceedings of the IASTED International Conference, (2001).

Jouve, Francois and Hanna, Khalil, "Computer Simulations of Refractive Surgery and Accomodation Mechanisms", IUTAM Symposium on Synthesis in Bio Solid Mechanics. Springer Netherlands, (2006).

Zhang, Hongwei, "Finite Element Modeling of the Cornea and its Application in the Refractive Surgery", A Study of Abberrations in the Human Eye by Zernike Phase Plate Precompensation and Finite Element Modeling Methods, Chapter 1, pp. 1-26, 2007, Heilongjiang, China.

* cited by examiner

FINITE ELEMENT MODELING OF THE CORNEA

FIELD OF THE INVENTION

The present invention pertains generally to systems and methods for biomechanically modeling the corneal structure in an eye of a patient. More particularly, the present invention pertains to finite element models that are based on diagnostic corneal data. The present invention is particularly, but not exclusively, useful as a finite element model that will predict changes in a corneal configuration resulting from a pre-determined Laser Induced Optical Breakdown (LIOB) of tissue in an actual cornea.

BACKGROUND OF THE INVENTION

A finite element model typically includes a plurality of discrete elements that are arranged to simulate a particular structure or environment. Importantly, each element in such a model can be individually pre-programmed to exhibit particular physical characteristics of the structure, or environment, that is being modeled. Of particular importance for the present invention is the structure for the cornea of an eye.

Anatomically, the microstructure for the cornea of an eye includes five identifiable layers of tissue. Proceeding in a posterior direction from the anterior surface to the posterior surface of the cornea, these layers are: 1) Epithelium, 2) Bowman's Capsule, 3) Corneal Stroma, 4) Descemet's membrane, and 5) Endothelium. Of these tissue layers, Bowman's capsule and the corneal stroma are, bio-mechanically, the most important for purposes of reshaping the cornea. Specifically, although it is relatively thin (~12 µm) Bowman's capsule is approximately five times stronger in tensile strength than the next strongest tissue, the corneal stroma. The corneal stroma, however, comprises approximately eighty percent of the cornea (~500 µm).

It happens that when modeling the cornea, only Bowman's capsule and the corneal stroma need be considered for most practical applications. In these models, and in line with the anatomical and biomechanical factors mentioned above, the stronger Bowman's capsule requires more finite elements than does the corneal stroma. It also requires higher stress scaling coefficients. As for boundary conditions on the finite element model, it is generally accepted that a sufficient approximation of an actual cornea can be made by pre-programming elements to represent the periphery of Bowman's capsule. Specifically, these peripheral elements can be effectively pre-programmed to represent a fixed attachment of the cornea to the limbus (sclera) of the eye.

In conjunction with recently developed laser surgical protocols, a finite element model gives promise of being able to effectively predict refractive surgery results. Specifically, U.S. Patent Applications for inventions respectively entitled "Method for Intrastromal Refractive Surgery", and "Computer Control for Bio-mechanical Alteration of the Cornea", both of which are assigned to the same assignee as the present invention, have addressed surgical protocols for reshaping the cornea. In accordance with disclosure from these applications, the protocols create weaknesses in stromal tissue that result in a redistribution of bio-mechanical stresses and strains in the cornea. With this redistribution, the objective is to then have intraocular pressure from the anterior chamber of the eye force a reshaping of the cornea for the purpose of correcting the refractive power of the cornea.

In light of the above, it is an object of the present invention to provide a finite element model that responds to the LIOB of corneal tissue, to thereby predict a consequent reshaping of the cornea. Yet another object of the present invention is to provide a system and a method for evaluating changes in the bio-mechanical stress-strain distributions within the cornea, in response to predetermined LIOB. Still another object of the present invention is to provide a system and method for simulating and modeling the reshaping of a cornea that is relatively simple to implement, is easy to use and is comparatively cost effective.

SUMMARY OF THE INVENTION

In accordance with the present invention, a system for simulating the reshaping of a model cornea requires use of a computer with finite element simulation software. Specifically, the computer is programmed with a finite element model having a plurality of discrete elements. A first group of these elements are pre-programmed to simulate biomechanical characteristics for Bowman's capsule of the cornea. And, a second group of elements are pre-programmed to simulate biomechanical characteristics for the corneal stroma. In the finite element model, the elements are arranged in layers, according to their group. For example, the finite element model will preferably have nine layers of elements wherein each layer has a substantially circular periphery. Further, three of these layers simulate Bowman's Capsule and include elements of the first group. The remaining six layers will then be used to simulate stromal tissue and will include elements of the second group.

In detail, the finite element model of the present invention defines an anterior surface and a posterior surface for the cornea. An axis is defined that is perpendicular to both surfaces and passes through respective apexes of the surfaces. In the finite element model, the curvatures of the anterior and posterior surfaces are approximated by a respective conic section that is expressed as:

$$z(x) = \frac{1}{e^2 - 1}[\sqrt{R^2 + x^2(e^2 - 1)} - R].$$

For the present invention, the radius of curvature, R, for the anterior surface is approximately 7.86 mm. R for the posterior surface, on the other hand is approximately 6.76 mm, and the eccentricity of the cornea, e, is 0.32.

Mathematically, within the finite element model, each element is three-dimensional and is defined by six tensors and their respective coefficients. In this case, for simulation of Bowman's Capsule and respectively for the stroma, coefficients for the pre-programmed elements of both the first and second groups are established according to diagnostic corneal data. Further, due to the greater elasticity of Bowman's Capsule, its stress-scaling coefficient ($C_{Bowman}$) is approximately five times greater than the stress-scaling coefficient for the stroma ($C_{stroma}$).

Additionally, elements along the periphery of the layers that are simulating Bowman's Capsule are pre-programmed for a boundary condition that represents a fixed attachment of Bowman's Capsule to the limbus (sclera) of the cornea being modeled. Also, elements in the finite element model are pre-programmed to replicate the presence of intraocular pressure against the posterior surface of the cornea. With all this in mind, the finite element model for the present invention is axisymmetric and is based on a nonlinearly elastic, slightly compressible, transversely isotropic formulation with an isotropic exponential Lagrangian strain-energy function based on:

$$W = \tfrac{1}{2}C(e^Q - 1) + C_{compr}(I_3 \ln I_3 - I_3 + 1)$$

and $$Q = b_{ff}E^2_{ff} + b_{xx}(E^2_{cc} + E^2_{ss} + E^2_{cs} + E^2_{sc}) + b_{fx}(E^2_{fc} + E^2_{cf} + E^2_{fs} + E^2_{sf})$$

Where:
   I are invariants,
   W is the strain potential (strain-energy function),
   C is stress-scaling coefficient,
   $C_{compr}$ is bulk modulus (kPa),
   E is strain,
   $b_{ff}$ is fiber strain exponent,
   $b_{xx}$ is transverse strain component, and
   $b_{fx}$ is fiber-transverse shear exponent.

In the operation of the present invention, the finite element model simulates cuts that are made only inside the stroma. These cuts may be either substantially parallel to the axis, or substantially perpendicular to the axis. In either case, designated biomechanical characteristics that are pre-programmed on selected element(s) of the finite element model are minimized. Specifically, minimization of the elements is accomplished by reducing coefficients for the pre-programmed biomechanical characteristics. Quantitatively, this reduction takes the selected coefficients into a range that is approximately eighty to ninety five percent less than their originally pre-programmed value. The model configuration that results in response to this reduction (minimization) is then measured and compared with actual surgical results. The entire process can then be repeated, as required.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
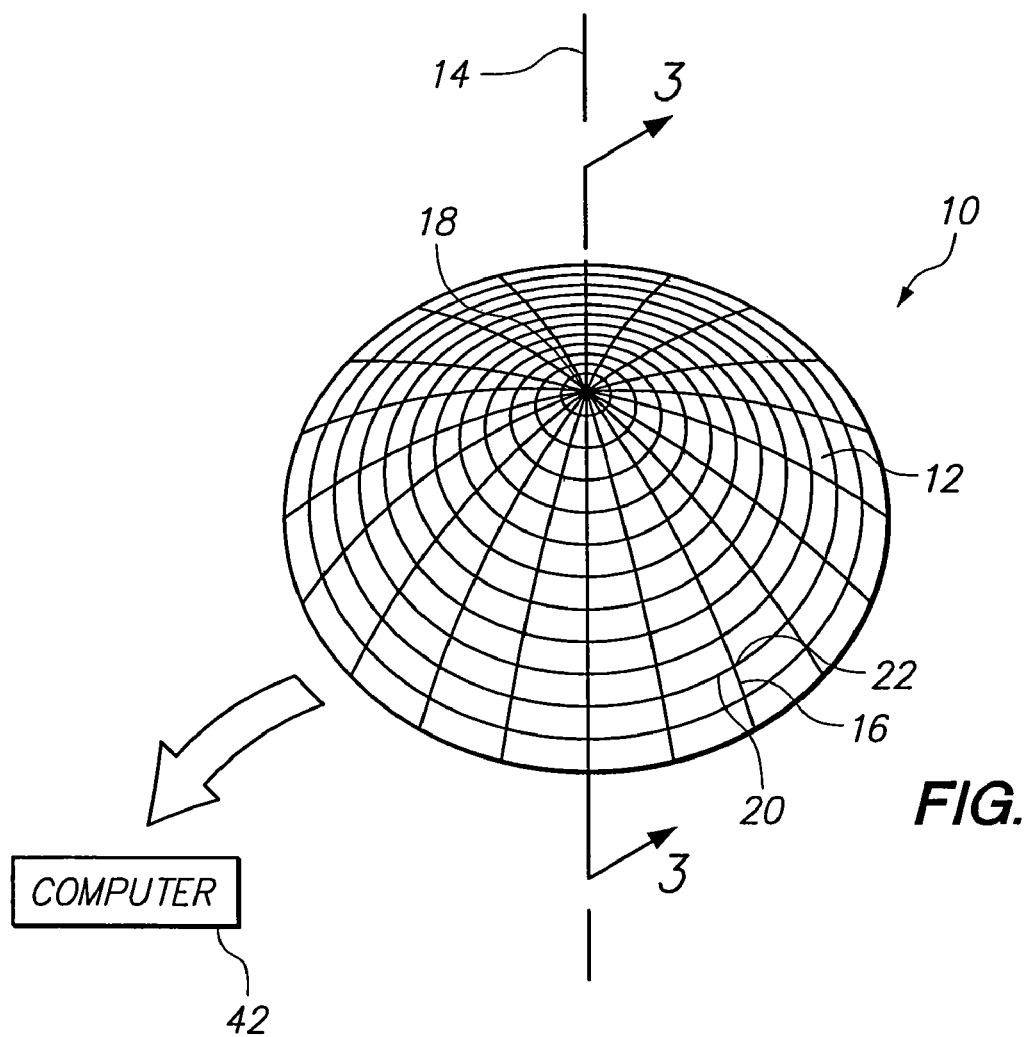
FIG. 1 is a perspective view of a layer of a finite element model in accordance with the present invention.

Referring initially to FIG. 1, a portion of a finite element model, generally designated 10, is shown in accordance with the present invention. The model 10 includes at least one layer 12, such as the one shown in FIG. 1. Preferably, however, it will include a plurality of layers 12, as more fully disclosed below. As will be appreciated with reference to FIG. 1, the model 10 defines an axis 14, and each layer 12 of the model 10 is, in part, defined by a plurality of lines 16 that radiate outwardly from the axis 14. Additionally, the layer 12 is shown with an apex 18, and the axis 14 is shown perpendicular to the layer 12 at the apex 18. Further, a plurality of rings 20 are centered on the axis 14, with each intersection of a line 16 with a ring 20 defining the location of an element 22. Thus, as shown, the finite element model 10 comprises a plurality of the elements 22.

Figure 2:
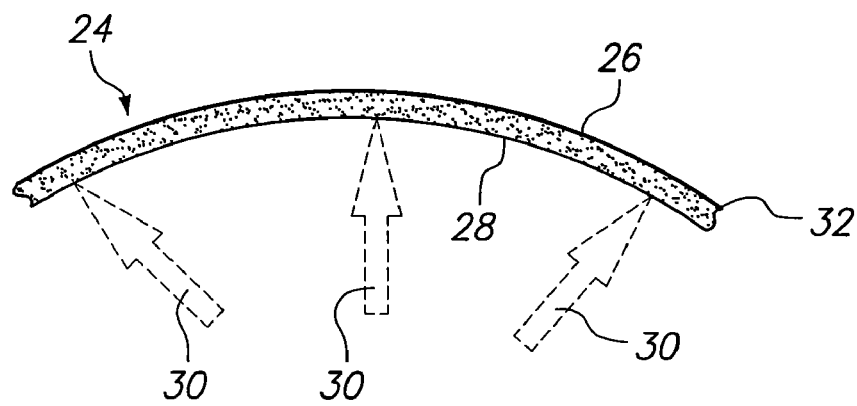
FIG. 2 is a representative cross-sectional view of a simulated cornea for use in the finite element model.

In FIG. 2 a simulated cornea for use in the finite element model 10 is shown and is generally designated 24. As shown, this simulated cornea 24 includes only a representative Bowman's Capsule 26 and a stroma 28. Further, intraocular pressure (IOP) exerted against the cornea in an actual eye (not shown), is indicated by the arrows 30. Also shown, is the boundary condition 32 that is pre-programmed into the finite element model 10 to replicate anatomical conditions at the interface between the cornea and the limbus (sclera) of an actual patient. For purposes of the present invention, this boundary condition 32 need only be established with elements 22 that are pre-programmed to replicate Bowman's Capsule 26.

Figure 3:
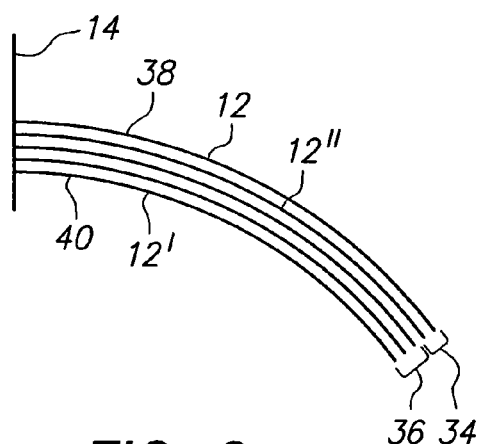
FIG. 3 is a cross-sectional view of a plurality of element lines, in a plurality of layers, in the finite element model as seen along the line 3-3 in FIG. 1.

FIG. 3 shows that the model 10 includes a plurality of different layers 12 (the layers 12' and 12" are only exemplary). FIG. 3 also shows a first plurality 34 of layers 12 having a first group of elements 22 that are pre-programmed to simulate biomechanical characteristics for Bowman's Capsule 26 in the simulated cornea 24. FIG. 3 also shows a second plurality 36 having a second group of elements 22 that are pre-programmed to simulate biomechanical characteristics in the corneal stroma 28 in the simulated cornea 24.

By way of example, the finite element model 10 preferably has nine layers 12. In these nine layers 12, the first (anterior) plurality 34 of layers 12 and elements 22 comprises three layers 12 that simulate Bowman's Capsule 26. The second (posterior) plurality 36 of layers 12 and elements 22 comprises six layers 12 and simulates stromal tissue 28 in the simulated cornea 24. Additional layers 12 of elements 22, in each plurality 34 and 36, are, of course, possible.

In detail, the finite element model 10 of the present invention defines an anterior surface 38 and a posterior surface 40 for the simulated cornea 24. The curvatures of the anterior surface 38 and the posterior surface 40 are approximated by a respective conic section that is expressed as:

$$z(x) = \frac{1}{e^2 - 1}\left[\sqrt{R^2 + x^2(e^2 - 1)} - R\right].$$

Specifically, the radius of curvature, R, for the anterior surface 38 is approximately 7.86 mm. R for the posterior surface 40, on the other hand, is approximately 6.76 mm. Also, the eccentricity of the cornea, e, is 0.32.

Within the finite element model 10, each element 22 is three-dimensional. Mathematically, each element 22 is defined by tensors, with respective coefficients corresponding to bio-mechanical stresses and strains. In this case, coefficients for the pre-programmed elements of both the first and second groups are established according to diagnostic corneal data. Also, in line with anatomical consideration, the stress-scaling coefficient for Bowman's Capsule 26 ($C_{Bowman}$) is approximately five times greater than the stress-scaling coefficient for the stroma 28 ($C_{stroma}$).

In greater detail, the finite element model 10 for the present invention is axisymmetric and is based on a nonlinearly elastic, slightly compressible, transversely isotropic formulation with an isotropic exponential Lagrangian strain-energy function based on:

$$W = \tfrac{1}{2}C(e^Q - 1) + C_{compr}(I_3 \ln I_3 - I_3 + 1)$$

and $$Q = b_{ff}E^2_{ff} + b_{xx}(E^2_{cc} + E^2_{ss} + E^2_{cs} + E^2_{sc}) + b_{fx}(E^2_{fc} + E^2_{cf} + E^2_{fs} + E^2_{sf})$$

Where:
- I are invariants,
- W is the strain potential (strain-energy function),
- C is stress-scaling coefficient,
- $C_{compr}$ is bulk modulus (kPa),
- E is strain,
- $b_{ff}$ is fiber strain exponent,
- $b_{xx}$ is transverse strain component, and
- $b_{fx}$ is fiber-transverse shear exponent.

As indicated in FIG. 1, for the operation of the present invention the finite element model 10 is programmed into a computer 42. For this purpose, the computer 42 must be capable of using finite element simulation software. Preferably, the software used is of a type similar to Continuity 6, which is distributed free for academic research by the National Biomedical Computation Resource.

Figure 4:
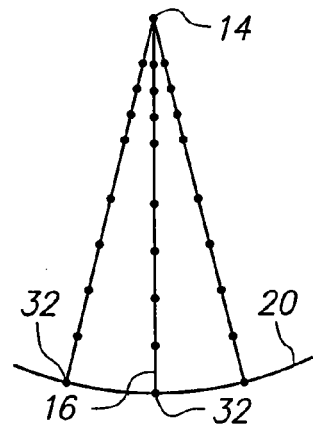
FIG. 4 is a top plan view of a plurality of element lines in a single layer of the finite element model.

By cross-referencing FIG. 1, with both FIG. 3 and FIG. 4, it will be appreciated that a plethora of coefficients for the finite element model 10 need to be pre-programmed into the computer 42. As noted above, these coefficients are mathematically determined for each element 22 of the model 10, and are based on diagnostic corneal data. The exact number of elements 22 that need to be programmed for the model 10 will depend on the particular application to be followed. In any event, once the coefficients have been pre-programmed, the operation then turns to simulating the effects of tissue cuts inside the stroma of an actual cornea. For the model 10, this simulation is accomplished within the stroma 28 of the simulated cornea 24. Thus, only elements 22 in the second plurality of layers 36 are affected.

In order to simulate cuts through tissue inside actual corneal stroma, the coefficients pertaining to selected elements 22 in layers 36 of the finite element model 10 are minimized. Specifically, minimization of the selected elements 22 is accomplished by reducing their coefficients into a range approximately between eighty to ninety five percent less than their originally pre-programmed value. The configuration of the model 10 that results in response to this reduction (minimization) is then measured. These measurements, in turn, can then be compared with surgical results for refinement of the surgical protocol.

Figure 5A:
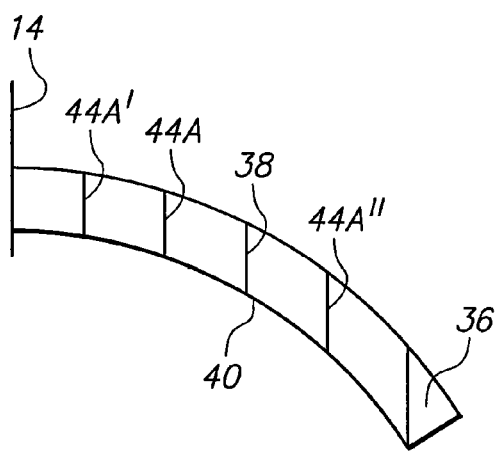
FIG. 5A illustrates representative stress lines of elements in FIG. 3 prior to operation of the finite element model.
Figure 5B:
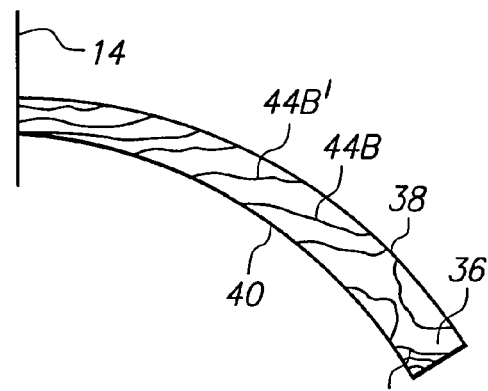
FIG. 5B illustrates representative stress lines of elements in FIG. 3 after operation of the finite element model.

An example of stress distribution changes within the stroma 28 of the simulated cornea 24 will, perhaps, be best appreciated by comparing FIG. 5A (a stress distribution in the model 10 before minimization of elements 22) with FIG. 5B (the resultant stress distribution after minimization of the elements 22). Specifically, FIG. 5A indicates that the entire model 10 (i.e. layers 34 and 36) is in a base condition wherein isostress lines 44a, 44a' and 44a" within the model 10 are exemplary, and correspond to diagnostic data taken from the cornea of an eye (not shown). For discussion purposes, this base condition is shown in FIG. 5A as having isostress lines 44a which are oriented substantially parallel to axis 14. FIG. 5B, on the other hand, shows isostress lines 44b that are induced by minimizing coefficients in the simulated procedure. Stated differently, the isostress lines 44b, 44b' and 44b" shown in FIG. 5B are exemplary of changes from the base condition shown by exemplary isostress lines 44a, 44a' and 44a" in FIG. 5A. The consequent reconfiguration of the simulated cornea 24 as a result of this redistribution is then shown in FIG. 6.

Figure 6:
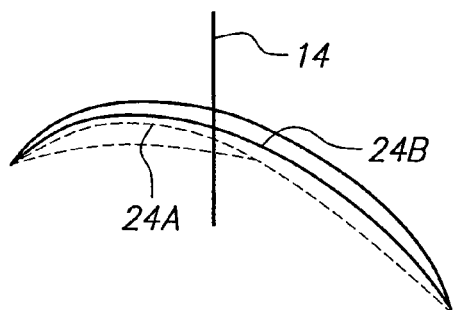
FIG. 6 shows superposed, representative configurations of the finite element model corresponding to stress lines illustrated in FIGS. 5A and 5B.

FIG. 6 shows changes in configuration for the simulated cornea 24 of the finite element model 10 that correspond to the resultant redistribution of isostress line 44 illustrated in FIG. 5B. Specifically, the configuration for simulated cornea 24a, shown in FIG. 6, corresponds to the base condition for stresses shown in FIG. 5A. Similarly, the configuration for simulated cornea 24b, also shown in FIG. 6, corresponds to the stress condition illustrated in FIG. 5B.

While the particular Finite Element Modeling of the Cornea as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for simulating a reconfiguration of a model cornea which comprises:
    a computer programmed with a finite element model, wherein the finite element model defines an anterior surface and a posterior surface for the cornea, with an axis perpendicular to the surfaces and passing through respective apexes of the surfaces, and further wherein the curvatures of the anterior and posterior surfaces are approximated by a respective conic section, and the finite element model includes a plurality of elements, wherein a first group of elements are pre-programmed with coefficients to simulate biomechanical characteristics for Bowman's capsule of the cornea and a second group of elements are pre-programmed with coefficients to simulate biomechanical characteristics for a stroma of the cornea, and further wherein the pre-programmed elements of the first and second groups are established for the finite element model according to diagnostic corneal data;
    a computer means for reducing coefficients of the finite element model into a range approximately eighty to ninety-five percent of the preprogrammed value to minimize designated biomechanical characteristics on at least one selected element to create a reconfigured model cornea; and
    a computer means for measuring the reconfigured model cornea.

2. A system as recited in claim 1 wherein the conic section for each surface is expressed as:

$$z(x) = \frac{1}{e^2 - 1}\left[\sqrt{R^2 + x^2(e^2 - 1)} - R\right]$$

3. A system as recited in claim 2 where:
    R for the anterior surface is approximately 7.86 mm;
    R for the posterior surface is approximately 6.76 mm; and
    e for the eccentricity of the cornea is 0.32.

4. A system as recited in claim 1 wherein each element is three dimensional and includes tensors having stress-strain coefficients.

5. A system as recited in claim 1 wherein the finite element model defines nine layers of elements wherein three of the layers include the first group of elements, and six of the layers include the second group of elements.

6. A system as recited in claim 1 wherein the first computer means simulates a cut inside the stroma, substantially parallel to the axis.

7. A system as recited in claim 1 wherein the first computer means simulates a cut inside the stroma, substantially perpendicular to the axis.

8. A system as recited in claim 1 wherein the finite element model is axisymmetric and is based on a nonlinearly elastic, slightly compressible, transversely isotropic formulation with an isotropic exponential Lagrangian strain-energy function based on:

$$W = \tfrac{1}{2}C(e^Q - 1) + C_{compr}(I_3 \ln I_3 - I_3 + 1)$$

and $$Q = b_{ff}E^2_{ff} + b_{xx}(E^2_{cc} + E^2_{ss} + E^2_{cs} + E^2_{sc}) + b_{fx}(E^2_{fc} + E^2_{cf} + E^2_{fs} + E^2_{sf})$$

Where:
  I are invariants,
  W is the strain potential (strain-energy function),
  C is stress-scaling coefficient,
  $C_{compr}$ is bulk modulus (kPa),
  E is strain,
  $b_{ff}$ is fiber strain exponent,
  $b_{xx}$ is transverse strain component, and
  $b_{fx}$ is fiber-transverse shear exponent.

9. A system as recited in claim 8 wherein the stress-scaling coefficient for Bowman's capsule ($C_{Bowman}$) is approximately five times greater than the stress-scaling coefficient for the stroma ($C_{stroma}$).

10. A system for simulating a reconfiguration of a model cornea which comprises:
  a finite element model having a plurality of individual elements, wherein each element is pre-programmed with coefficients for biomechanical characteristics based on diagnostic corneal data to collectively replicate biomechanical properties of the cornea, and to represent the cornea in a first configuration wherein a first group of elements are pre-programmed elements to simulate biomechanical characteristics for Bowman's capsule of the cornea and a second group of elements are pre-programmed elements to simulate biomechanical characteristics for a stroma of the cornea, and further wherein the finite element model defines an anterior surface and a posterior surface for the cornea, with an axis perpendicular to the surfaces and passing through respective apexes of the surfaces, and further wherein the curvatures of the anterior and posterior surfaces are approximated by a respective conic section expressed as:

$$z(x) = \frac{1}{e^2 - 1}\left[\sqrt{R^2 + x^2(e^2 - 1)} - R\right].$$

Where:
    R for the anterior surface is approximately 7.86mm;
    R for the posterior surface is approximately 6.76mm;
    e for the eccentricity of the cornea is 0.32;
  a computer means for reducing the coefficients of the finite element model into a range approximately eighty to ninety-five percent of the preprogrammed value to minimize designated biomechanical characteristics on a plurality of selected elements to create a reconfigured model cornea; and
  a computer means for measuring the reconfigured model cornea.

11. A system as recited in claim 10 wherein the finite element model is axisymmetric and is based on a nonlinearly elastic, slightly compressible, transversely isotropic formulation with an isotropic exponential Lagrangian strain-energy function based on:

$$W = \tfrac{1}{2}C(e^Q - 1) + C_{compr}(I_3 \ln I_3 - I_3 = 1)$$

and $$Q = b_{ff}E^2_{ff} + b_{xx}(E^2_{cc} + E^2_{ss} + E^2_{cs} + E^2_{sc}) + b_{fx}(E^2_{fc} + E^2_{cf} + E^2_{fs} + E^2_{sf})$$

Where:
  I are invariants,
  W is the strain potential (strain-energy function),
  C is stress-scaling coefficient,
  $C_{compr}$ is bulk modulus (kPa),
  E is strain,
  $b_{ff}$ is fiber strain exponent,
  $b_{xx}$ is transverse strain component,
  $b_{fx}$ is fiber-transverse shear exponent, and
wherein the stress-scaling coefficient for Bowman's capsule ($C_{Bowman}$) is approximately five time greater than the stress-scaling coefficient for the stroma ($C_{stroma}$).

12. A system as recited in claim 10 wherein the finite element model defines nine layers of elements wherein three of the layers include the first group of elements and six layers include the second group of elements.

13. A system as recited in claim 10 wherein elements to be minimized are selected from the second group.

14. A method for using a computer to simulate a reconfiguration of a cornea which comprises the steps of:
  creating a finite element model comprising a plurality of elements;
  pre-programming the computer with a first plurality of the elements with coefficients to simulate biomechanical characteristics for Bowman's capsule of the cornea and a second plurality of the elements with coefficients to simulate biomechanical characteristics for a stroma of the cornea, wherein the pre-programmed elements are established for the finite element model according to diagnostic corneal data;
  minimizing biomechanical characteristics on selected elements by reducing coefficients into a range approximately eighty to ninety-five percent of the preprogrammed value to create a reconfigured cornea;
  measuring the reconfigured cornea in response to the minimizing step; and
  repeating the minimizing and measuring steps, as required.

15. A method as recited in claim 14 wherein the finite element model defines an anterior surface and a posterior surface for the cornea, with an axis perpendicular to the surfaces and passing through respective apexes of the surfaces, and further wherein the curvatures of the anterior and posterior surfaces are approximated by a respective conic section expressed as:

$$z(x) = \frac{1}{e^2 - 1}\left[\sqrt{R^2 + x^2(e^2 - 1)} - R\right].$$

* * * * *